US010228317B1

(12) United States Patent
Brundage et al.

(10) Patent No.: US 10,228,317 B1
(45) Date of Patent: Mar. 12, 2019

(54) MULTIPLEXED MICROFLUIDIC CELL SORTING USING LASER INDUCED CAVITATION BUBBLES

(71) Applicant: Verily Life Sciences LLC, Mountain View, CA (US)

(72) Inventors: Michael Brundage, San Francisco, CA (US); Supriyo Sinha, Menlo Park, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 0 days.

(21) Appl. No.: 15/656,154

(22) Filed: Jul. 21, 2017

Related U.S. Application Data (60) Provisional application No. 62/379,489, filed on Aug. 25, 2016.

(51) Int. Cl.
*G01N 15/14* (2006.01)
*B01L 3/00* (2006.01)
(Continued)

(52) U.S. Cl.
CPC .... *G01N 15/1436* (2013.01); *B01L 3/502715* (2013.01); *B01L 3/502761* (2013.01);
(Continued)

(58) Field of Classification Search
CPC ......... B01L 3/502761; B01L 3/502715; B01L 3/502753; B01L 2300/0877; B01L 3/502746; B01L 3/502784; B01L 2400/0421; B01L 2400/0436; G01N 2015/149; G01N 2015/1006; G01N 15/1459; G01N 15/1434; G01N 15/0205; G01N 15/1436; G01N 15/147; G01N 2201/061; G01N 2015/0288; G01N 2015/1481; G01N 35/08; G01N 15/1475;
(Continued)

(56) References Cited

U.S. PATENT DOCUMENTS

| 8,658,418 B2 * | 2/2014 | Daridon | C12M 1/34 |
| | | | 435/288.5 |
| 9,594,071 B2 * | 3/2017 | Hart | G01N 33/4833 |

(Continued)

*Primary Examiner* — Taeho Jo
(74) *Attorney, Agent, or Firm* — Christensen O'Connor Johnson Kindness PLLC (57) ABSTRACT

Systems and methods for sorting particles are described. In one implementation, a system for sorting particles include a microfluidic device, a detection system, and an optical switching system. The microfluidic device includes a sample channel for passing through the particles in a fluid medium, a plurality of output channels fluidly connected to the sample channel at a plurality of junctions, and an actuation channel. The detection system detects a particle passing through the sample channel. The optical switching system deflects the particle to a target output channel based on results detected by the detection system. The optical switching system includes a modulation device configured to direct a laser pulse to an actuation region in the actuation channel corresponding to the target output channel. Advantageously, the systems and methods allow for accurate and dynamic sorting of a mixture of cells into a plurality of subpopulations using a simple microfluidic device.

35 Claims, 6 Drawing Sheets

(51) Int. Cl.
*G01N 15/00* (2006.01)
*G01N 15/10* (2006.01)

(52) U.S. Cl.
CPC ..... *G01N 15/1459* (2013.01); *G01N 15/1484* (2013.01); *B01L 2200/0652* (2013.01); *B01L 2200/143* (2013.01); *B01L 2300/0654* (2013.01); *B01L 2300/0864* (2013.01); *G01N 2015/0065* (2013.01); *G01N 2015/1006* (2013.01); *G01N 2015/149* (2013.01)

(58) Field of Classification Search
CPC ............ G01N 1/20; G01N 2015/1438; G01N 2021/3595; G01N 21/1702
USPC ....................................................... 250/461.1
See application file for complete search history.

(56) References Cited

U.S. PATENT DOCUMENTS

| | | | | |
|---|---|---|---|---|
| 2002/0181837 A1* | 12/2002 | Wang | ........................ | H05H 3/04 385/16 |
| 2004/0067167 A1* | 4/2004 | Zhang | .................... | G01N 15/147 422/82.05 |
| 2005/0164158 A1* | 7/2005 | Wang | ........................ | H05H 3/04 435/2 |
| 2009/0107262 A1* | 4/2009 | Hashimoto | ........ | B01L 3/502738 73/863.11 |
| 2011/0001963 A1* | 1/2011 | Durack | .............. | G01N 15/1434 356/301 |
| 2011/0030808 A1* | 2/2011 | Chiou | ............... | B01L 3/502738 137/13 |
| 2011/0177547 A1* | 7/2011 | Xia | .................... | B01L 3/502738 435/34 |
| 2012/0236299 A1* | 9/2012 | Chiou | ............... | B01L 3/502715 356/301 |
| 2013/0302884 A1* | 11/2013 | Fowler | ................... | C12Q 1/686 435/287.2 |
| 2014/0008307 A1* | 1/2014 | Guldiken | .......... | B01L 3/502761 210/748.05 |
| 2015/0328637 A1* | 11/2015 | Perrault, Jr. | ...... | B01L 3/502738 435/287.1 |
| 2015/0352597 A1* | 12/2015 | Deshpande | ............... | F15C 5/00 209/577 |
| 2016/0296933 A1* | 10/2016 | Chiou | ............... | B01L 3/502738 |
| 2018/0031476 A1* | 2/2018 | Duer | .................... | G01N 21/648 |
| 2018/0067038 A1* | 3/2018 | Fathollahi | ............. | G01N 15/06 |

* cited by examiner

MULTIPLEXED MICROFLUIDIC CELL SORTING USING LASER INDUCED CAVITATION BUBBLES

CROSS REFERENCE TO RELATED APPLICATION

This application claims the benefit of U.S. Provisional Application No. 62/379,489 filed on Aug. 25, 2016, the contents of which are incorporated herein by reference.

BACKGROUND

Technical Field

The present disclosure generally relates to the field of systems and methods for flow cytometry. More particularly, and without limitation, the disclosed embodiments relate to microfluidic systems and methods for sorting particles and/or cells.

Background Description

Flow cytometry offers the ability to detect subpopulations of cells in heterogeneous mixtures of cells in various applications, such as biomedical research, diagnosis, drug screening, and clinical practice. To further analyze the detected cells, some technologies, such as fluorescence-activated cell sorting (FACS), allow for sorting a heterogeneous mixture of cells into two or more subpopulations. The sorted subpopulations can be analyzed by various analytical techniques, such as gene expression profiling, DNA sequencing, and high content image analysis. Cell sorting using traditional flow cytometers, such as commercial FACS machines, are generally expensive and complex, and are typically offered by central facilities that provide sterilization, filtering, and other auxiliary systems for using these machines.

Compared to traditional flow cytometers, microfluidic flow cytometers offer smaller, simpler, and less expensive devices that provide the capability to use less sample and reagents to detect, analyze, and sort cells, and thus allow for point-of-care uses. For example, some microfluidic fluorescence-activated cell sorters based on dielectrophoresis use electrostatic deflection to sort cells enclosed in aerosol droplets. Other microfluidic fluorescence-activated cell sorters use acoustic or mechanical actuation to achieve cell sorting. Microfluidic systems using these approaches typically allow for sorting cells into two or four different output channels, one of which may be a waste channel. However, analytical samples may have a greater number of distinct subpopulations of particles or cells to be more desirably sorted and analyzed. Therefore, there is a need for methods and systems that allow for multiplexed sorting of cells to large number of output channels in a microfluidic device.

SUMMARY

The embodiments of the present disclosure provide systems and methods for achieving multiplexed cell sorting. Advantageously, the exemplary embodiments allow for accurate and dynamic sorting of a mixture of cells into a plurality of subpopulations using a simple microfluidic device. Different subpopulations of cells in the mixture can be sorted into different output channels of the microfluidic device based on detected features of the cells.

According to an exemplary embodiment of the present disclosure, a system for sorting particles is described. The system may include a microfluidic device, a detection system, and an optical switching system. The microfluidic device may include a sample channel for passing through the particles in a fluid medium, a plurality of output channels fluidly connected to the sample channel at a plurality of junctions, and an actuation channel. The detection system may detect a particle passing through the sample channel. The optical switching system may deflect the particle to a target output channel based on results detected by the detection system. The optical switching system may include a modulation device. The modulation device may be configured to direct a laser pulse from the pulsed laser source to an actuation region in the actuation channel corresponding to the target output channel.

According to a further embodiment of the present disclosure, a system for sorting particles is described. The system may include a microfluidic device, a detection system, and an optical switching system. The microfluidic device may include a sample channel for passing through the particles in a fluid medium, a plurality of output channels fluidly connected to the sample channel at a plurality of junctions, and an actuation channel. The detection system may detect a particle passing through the sample channel. The optical switching system may deflect the particle to a target output channel based on results detected by the detection system. The optical switching system may include an acousto-optic modulator. The acousto-optic modulator may be configured to direct a laser pulse from the pulsed laser source to an actuation region in the actuation channel corresponding to the target output channel.

According to a yet further exemplary embodiment of the present disclosure, a method sorting particles is described. The method may include the step of receiving a fluid medium containing the particles by a microfluidic device. The microfluidic device may include a sample channel for passing through the particles, a plurality of output channels fluidly connected to the sample channel at a plurality of junctions, and an actuation channel. The method may further include the steps of detecting a particle passing through the sample channel using a detection system at a first time point, determining a target output channel based on results detected by the detection system, directing a laser pulse to an actuation region in the actuation channel corresponding to the target output channel at a second time point, and deflecting the particle to the target output channel by inducing a cavitation bubble that expands in the actuation region using the laser pulse.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

DETAILED DESCRIPTION

The disclosed embodiments relate to systems and methods for sorting particles. Advantageously, the exemplary embodiments allow for deflecting a particle towards a suitable target output channel in a microfluidic device based on detected features of the particle, thereby allowing for multiplexed sorting of different subpopulations of particles in a heterogeneous mixture. Embodiments of the present disclosure may be implemented in a flow cytometer, e.g., a microfluidic fluorescence-activated cell sorting (FACS) system. Alternatively, embodiments of the present disclosure may be implemented in a customized system built using customized microfluidic devices and/or optical elements.

According to an aspect of the present disclosure, a system is provided for multiplexed sorting of particles. The system includes a microfluidic device. The microfluidic device may include a sample channel for receiving a flow of fluid medium containing the particles to be sorted, a plurality of output channels for receiving and/or collecting the particles, and an actuation channel for actuating deflection of particles passing through the sample channel towards the output channels. The sample channel, actuation channel, and output channels are in fluid connection.

According to an aspect of the present disclosure, the system includes a detection system. The detection system may perform one or more types of optical detection of the particles passing through the sample channel of the microfluidic device of the system. The detection system may include at least one illumination source, e.g., a laser, at least one photodetector, at least one optical element for directing and/or focusing the illumination to particles passing through the sample channel, and at least one optical element for collecting light from the particles. In some embodiments, the particles are labeled with one or more fluorescent labels, and the detection system may generate detection results based on the detected fluorescent light from the particles. Alternatively or additionally, the detection system may generate detection results based on the detected scattered light from the particles.

According to an aspect of the present disclosure, the system includes an optical switching system for deflecting the particles passing through the sample channel towards target output channels. The optical switching system uses pulsed-laser-induced cavitation in the actuation channel as a mechanism to actuate the deflection. In some embodiments, the optical system may include a pulsed laser as a source of laser pulses. In other embodiments, the optical system may include a continuous wave laser, a pulsing device for generating laser pulses from the continuous wave laser. The optical switching system further uses a modulation device for dynamically modulating the actuation at selected target actuation regions in the actuation channel of the microfluidic device. The selected target actuation regions correspond to a target output channels of the microfluidic device for receiving the deflected particles.

In certain aspects, the optical switching system may include a pulsed laser and an acousto-optic modulator (AOM) as the modulation device. The AOM may rapidly modulate angular deflection of a pulsed laser beam to a target actuation region in the actuation channel corresponding to a target output channel. Advantageously, a laser pulse and the deflection of the laser pulse may be synchronized such that the pulsed laser beam can be flexibly directed to different target actuation regions without activating undesired actuation regions during the dynamic modulation.

In certain aspects, the optical switching system may include a continuous wave laser beam and an AOM. The AOM may rapidly modulate the intensity and the angular deflection of a laser beam. For example, the AOM may modulate the intensity of a continuous wave laser beam to generate a laser pulse of a predetermined duration. The AOM may also deflect the propagation of the generated laser pulse to a target actuation region in the actuation channel corresponding to a target output channel. Advantageously, the laser beam can be pulsed and deflected simultaneously by the AOM such that the laser pulses can be directed to different target actuation regions without activating undesired actuation regions during the dynamic modulation.

In certain aspects, the optical switching system may include a scanning mirror assembly for deflecting, scanning, and/or directing a laser beam or a laser pulse. In such instances, the optical switching system may include a pulsed laser and the scanning mirror assembly may direct a laser pulse to a suitable actuation region in the actuation channel. In some embodiments, the scanning mirror assembly may be a galvo mirror assembly or a polygon mirror assembly that allows for fast and accurate direction of the laser pulse. Alternatively, the optical switching system may include a continuous wave laser and an AOM for generating laser pulses. For example, the AOM may modulate the intensity of a continuous wave laser beam to generate a laser pulse and the scanning mirror assembly may deflect the laser pulse to the suitable target actuation region.

According to an aspect of the present disclosure, the system may include a controller that controls the timing of the detection and deflection of the particles passing through the sample channel, thereby allowing for accurate and/or high-throughput sorting. The controller is connected to the detection system and the optical switching system. In some embodiments, the controller may be a part of the detection system or a part of the optical switching system. The controller may advantageously control the optical switching system to actuate a target actuation region in the actuation channel at a suitable time point such that a particle passing through the sample channel is deflected at a suitable location, corresponding to the target output channel determined based on the results of detection of the particle.

Advantageously, the optical switching system allows for using a single laser to achieve dynamic and multiplexed particle sorting, thereby reducing the complexity and the cost of the cell sorting system. In such configuration, the total power of a laser pulse may be focused and used for the deflection of a particle, thereby increasing the efficiency of using the power of the laser. The optical switching system may further reduce the complexity of the microfluidic device by optically deflecting the particles to target output channels, thereby reducing the complexity of the microfluidic device, e.g., by eliminating the need for electrodes or actuation elements in the microfluidic device. Additionally, the modulation device of the optical switching system can be reconfigured to adjust the deflection angles, allowing the scanning or deflection of the laser pulse to be flexible and scalable for microfluidic devices having different two-dimensional or three-dimensional layouts of flow channels.

As described herein, embodiments of the present disclosure may allow sorting of various types of particles, such as cells, viruses, droplets, synthesized particles, etc. The particles may be tagged or labeled with optical labels that emit light with characteristic spectrum, indicating one or more biological, chemical, and/or physical features of the particles. Additionally, as described herein, a fluid medium may refer to a liquid solvent, water, buffer, etc.

Reference will now be made in detail to embodiments and aspects of the present disclosure, examples of which are illustrated in the accompanying drawings. Elements in the drawings are not drawn to scale.

Figure 1:
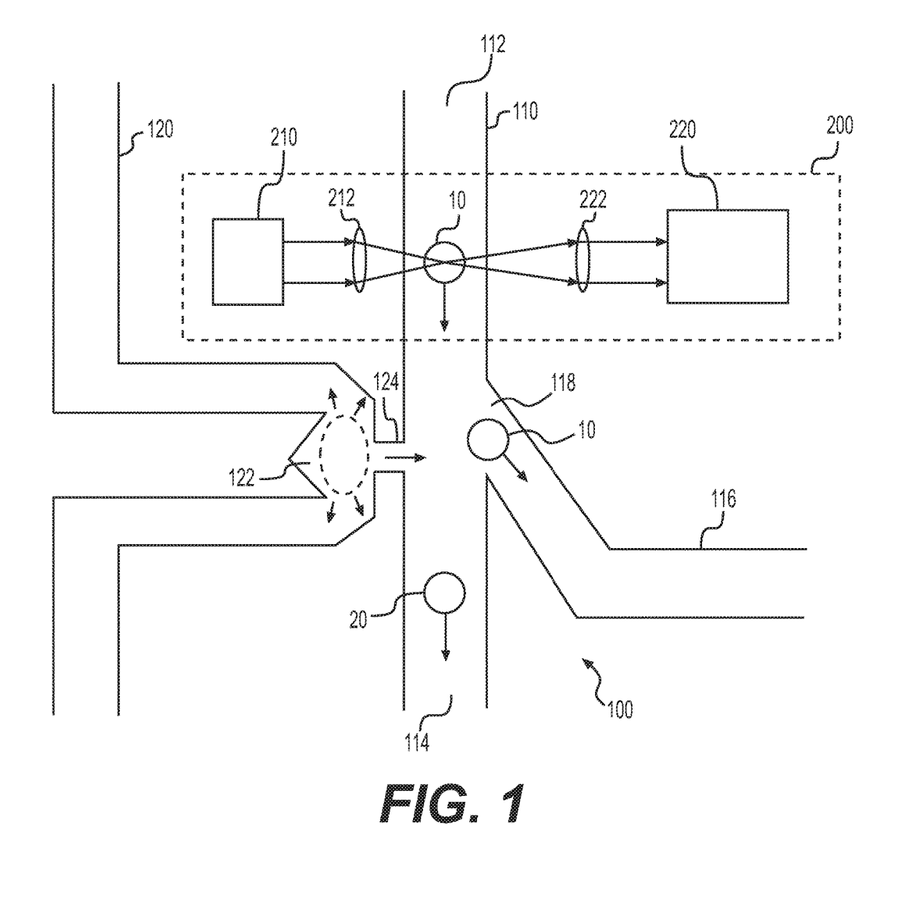
FIG. 1 is a schematic representation of particle sorting using pulsed-laser-induced cavitation.

FIG. 1 is a schematic representation illustrating particle sorting using pulsed-laser-induced cavitation in a microfluidic device. As shown in FIG. 1, a microfluidic device 100 may include a sample channel 110, an actuation channel 120, and one or more output channels 116. Sample channel 110 may have an inlet 112 for receiving a fluid medium carrying a plurality of particles, such as particles 10 desired to be sorted and particles 20 that do not need to be sorted. Sample channel 110 may have an outlet 114 for collecting unsorted particles 20 and at least some of the fluid medium.

As shown in FIG. 1, output channel 116 fluidly connects to sample channel 110 at a junction 118. Actuation channel 120 fluidly connects to sample channel via a nozzle 124. Nozzle 124 is located near junction 118 such that upon actuation, a fluid flow ejecting from nozzle 124 would push particle 10, thereby deflecting particle 10 towards junction 118 and then into output channel 116.

To determine whether a particle in the fluid medium passing through sample channel 110 needs to be sorted into output channel 116, a detection system 200 may be used. Detection system 200 may include an illumination source 210 for illumination light to the particle passing through sample channel 110 and a photodetector 220 for detecting the light from the illuminated particle. In some embodiments, illumination source 210 is a laser. Detection system 200 may further include at least one lens 212 focusing the light from illumination source 210 to the particle and/or at least one lens 222 for collecting light from the particle illuminated while passing sample channel 110. Detection system 200 may further include electronic circuits that convert detected light by photodetector 220 to detection results indicating the features of the particle. The detection results are then used for determining whether the particle is desired to be sorted into output channel 116. For example, as shown in FIG. 1, if the detection results of particle 10 indicates that the particle belongs to a subpopulation to be sorted to output channel 116, particle 10 is then deflected towards junction 118 and output channel 116.

As described herein, the detection results may be derived from one or more types of optical detection of detection system 200, such as forward scatter collection (FSC), side scatter collection (SSC), and one or more fluorescence collections (FL). Detection system 200 may further include other suitable optical elements, such as one or more dichroic mirrors, filters, beam dumps, etc.

Based on the detection results of particle 10 by detection system 200, an actuation region 122 of actuation channel 120 may be activated to deflect particle 10 towards output channel 116. For example, a fluid medium, such as water, may flow through actuation channel 120 while the particles pass through sample channel 110. When particle 10 is detected by detection system 200 upstream junction 118, based on the detection result, a laser pulse may be triggered and focused onto actuation region 122 in actuation channel 120 after a suitable time delay. The laser pulse induces liquid water flowing in actuation channel 120 to vaporize rapidly through nonlinear optical absorption at actuation region 122. As shown in FIG. 1, this creates localized hot plasma that vaporizes water to generate an explosive cavitation bubble at actuation region 122. The cavitation bubble expands and displaces the surrounding fluid rapidly, creating a high speed liquid jet flowing through nozzle 124 into sample channel 110. This liquid jet deflects or pushes particle 10 towards junction 118 and output channel 116. The expansion and collapse of the induced cavitation bubble can be very fast, e.g., on nanosecond or femtosecond time scale depending on the duration of the laser pulse. Advantageously, nozzle 124 focuses the deflecting liquid jet, narrows the activated region in sample channel 110, and reduces the disturbance to other particles passing in sample channel 110. The induced liquid jet may stop after the cavitation bubble collapses. Particles that do not need to be sorted based on the detection result, e.g., particle 20, are directed into outlet 114 of sample channel 110.

Advantageously, the expansion and collapse of the induced cavitation bubble occur for very short periods of time, allowing for transiently deflecting a particle to be sorted towards output channel 116. The dimension and location of nozzle 124, and the focus location, energy, and duration of the laser pulse may be adjusted to control the speed, volume, and location of the induced liquid jet, and to increase the speed and accuracy for deflecting one or more particles as needed to output channel 116.

The particle sorting as shown in FIG. 1 allows for sorting one subpopulation of particles. To achieve multiplexed sorting of a mixture of particles with large number of subpopulations, embodiments of the present disclosure include an optical switching system as described below in reference to FIGS. 2A-2C.

Figure 2A:
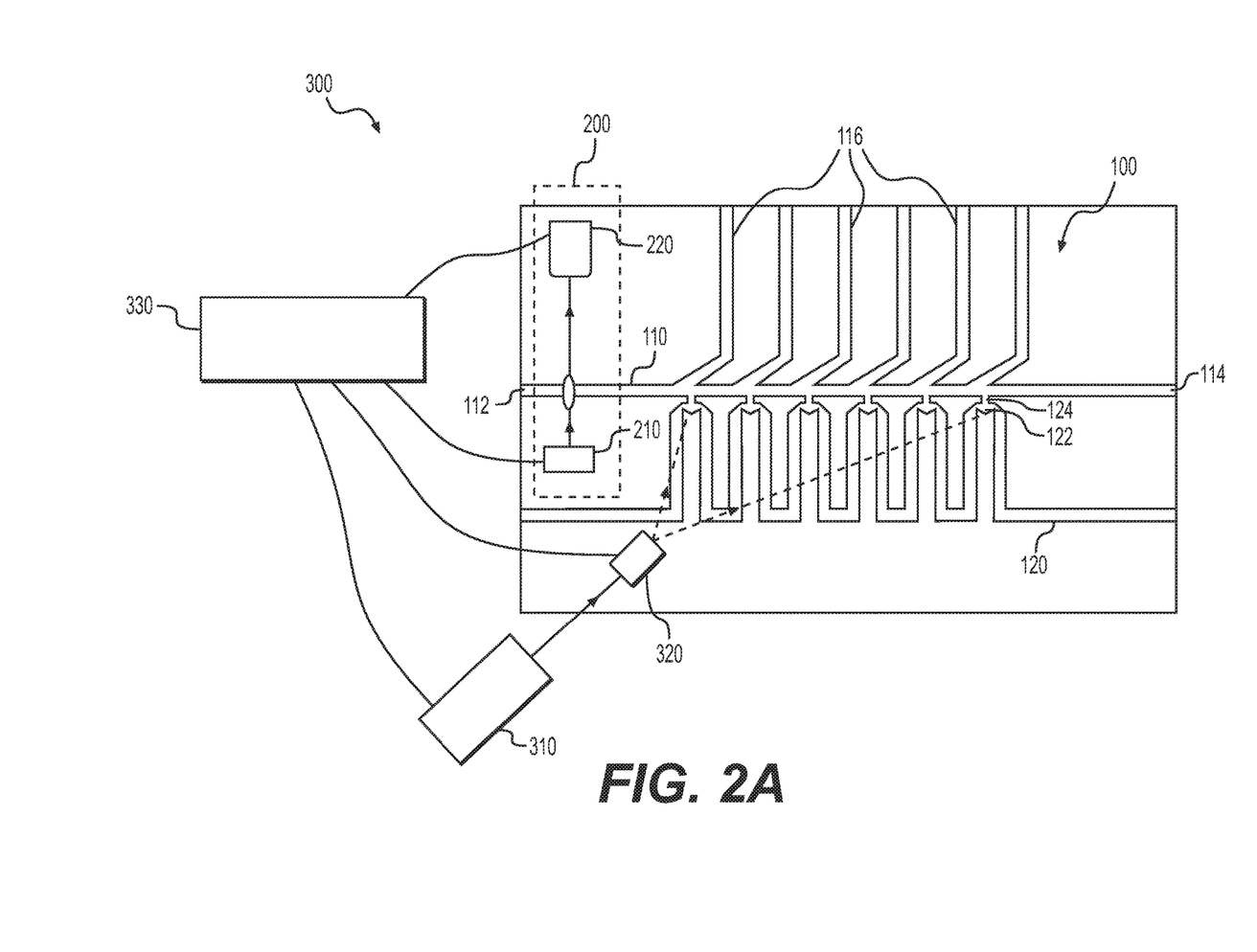
FIG. 2A is a schematic representation of an exemplary system for sorting particles, according to embodiments of the present disclosure.

FIG. 2A is a schematic representation of an exemplary system 300 for sorting particles. As shown in FIG. 2A, system 300 may include a microfluidic device 100 and an optical switching system. Microfluidic device 100 may have a sample channel 110, a plurality of output channels 116, and an actuation channel 120 with a plurality of actuation regions 122 and nozzles 124 corresponding to the plurality of output channels 116 respectively. The optical switching system includes a laser 310, a modulation device, e.g., an acousto-optic modulator (AOM) 320, and a computing device or a controller 330.

Functions and the working principles of system 300 for multiplexed sorting of particles passing through the sample channel 110 towards target output channels 116 of microfluidic device 100 are described in detail below.

In some embodiments, laser 310 of the optical switching system is a continuous wave laser and outputs a continuous laser beam. AOM 320 may pulse the continuous laser beam received from laser 310, generating laser pulses with predetermined duration. The pulsing of the continuous laser beam by AOM 320 may be controlled by controller 330. For example, controller 330 may trigger the generation of a laser pulse with a predetermined duration by AOM 320 at a suitable time point.

To deflect a particle passing sample channel 110, AOM 320 may direct the generated laser pulse to an actuation region 122 in the actuation channel 120 that corresponds to a target output channel 116 for the particle. For example, AOM 320 may have a piezoelectric transducer that modulate the angular deflection of the laser beam received from laser 310. The angular deflection may be linearly proportional to the acoustic frequency of the acoustic wave generated by the piezoelectric transducer. For example, increasing the acoustic frequency may increase the deflection angle of the laser beam.

In other embodiments, laser 310 is a pulsed laser and outputs a pulsed laser beam. To deflect a particle passing sample channel 110, AOM 320 may direct a pulsed laser beam received from laser 310 to an actuation region 122 in the actuation channel 120 that corresponds to a target output channel 116 or the particle.

As described herein, the number of output channels 116 for collected sorting particles may be determined by various factors, such as the dimensions of the channels, the range of angular deflection of a laser beam provided by the modulation device, and the scanning range on microfluidic device 100. For example, the range of angular deflection of a laser beam using AOM 320 may be determined by the acoustic property of AOM 320. The scanning range on microfluidic device 100 may be determined by the range of angular deflection provided by the modulation device and the distance between the modulation device and microfluidic device 100. To increase the range of deflection of the laser beam, thereby increasing the number of output channels for sorting particles, other suitable scanning devices or methods may be used. For example, the modulation device of system 300 may be a scanning mirror assembly.

Figure 2B:
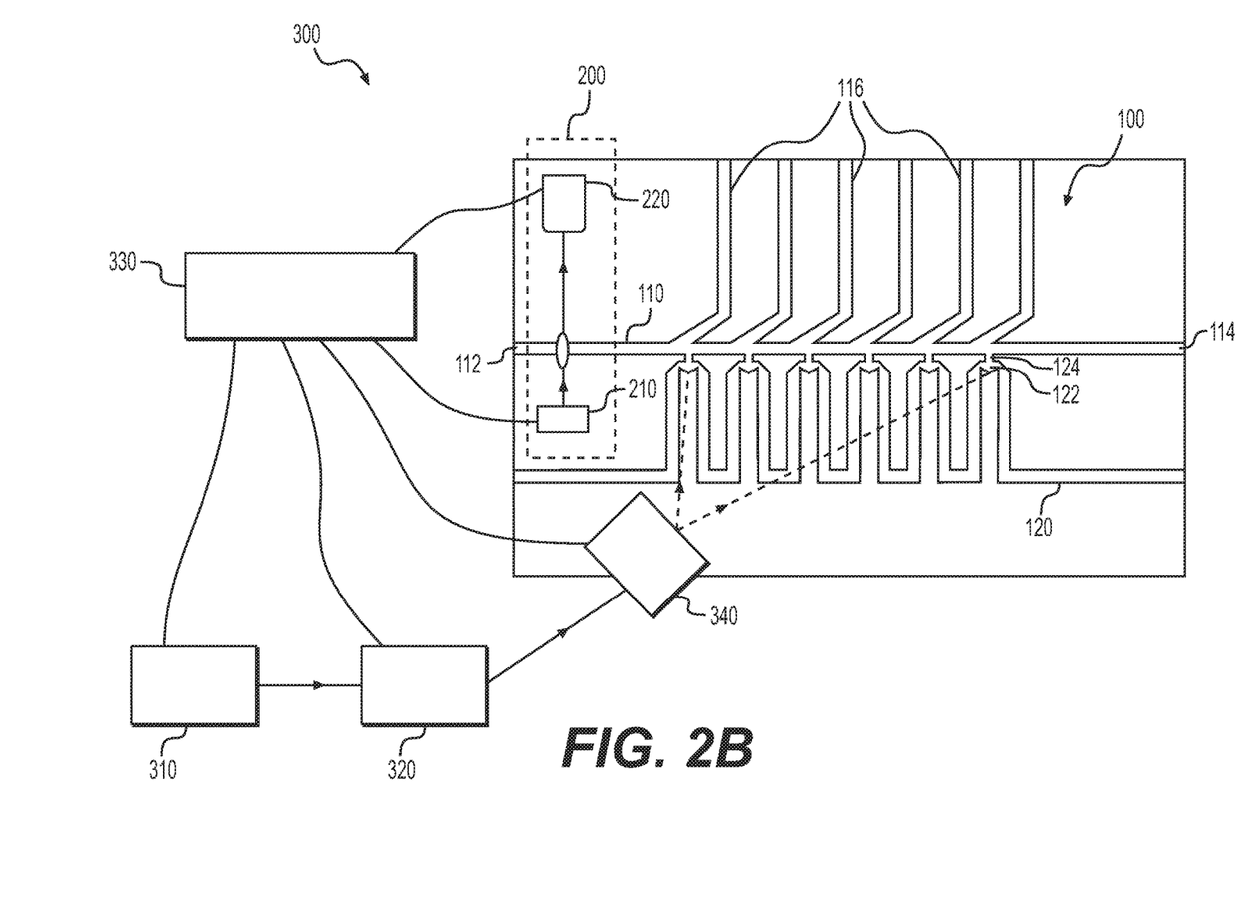
FIG. 2B is a schematic representation of another exemplary system for sorting particles, according to embodiments of the present disclosure.

FIG. 2B is a schematic representation of another exemplary system 300 for sorting particles. As shown in FIG. 2B, the modulation device of system 300 is a galvo mirror assembly 340. As described above, if laser 310 is a pulsed laser, controller 330 may synchronize the triggering of a laser pulse and the deflecting of the laser pulse such that a suitable actuation region corresponding to a target output channel 116 to sort a particle into is activated. Alternatively, if laser 310 is a continuous wave laser, system 300 may include a AOM 320 for generating a pulsed laser beam, e.g., by modulating the intensity of the laser beam. The modulation of the laser beam may be synchronized with the scanning of galvo mirror assembly.

In some embodiments, galvo mirror assembly 340 is a single-axis scanning assembly that allows for directing a laser beam across a predetermined linear range on microfluidic device 100. In other embodiments, galvo mirror assembly 340 is a dual-axis scanning assembly that allows for directing a laser beam across a two-dimensional area on microfluidic device 100. The size, type, scanning range, and scanning speed of galvo mirror assembly 340 may be selected based on the design of the microfluidic device 100 and the particular application of system 300.

Galvo mirror assembly 340 may allow for a larger scanning range, e.g., about tens of degrees of angular deflection or several millimeters on microfluidic device 100, at a high scanning rate, e.g., in kilohertz range. In such instances, galvo mirror assembly 340 may continually scanning back and forth (e.g., at a resonant frequency) in one or two dimensions.

Figure 2C:
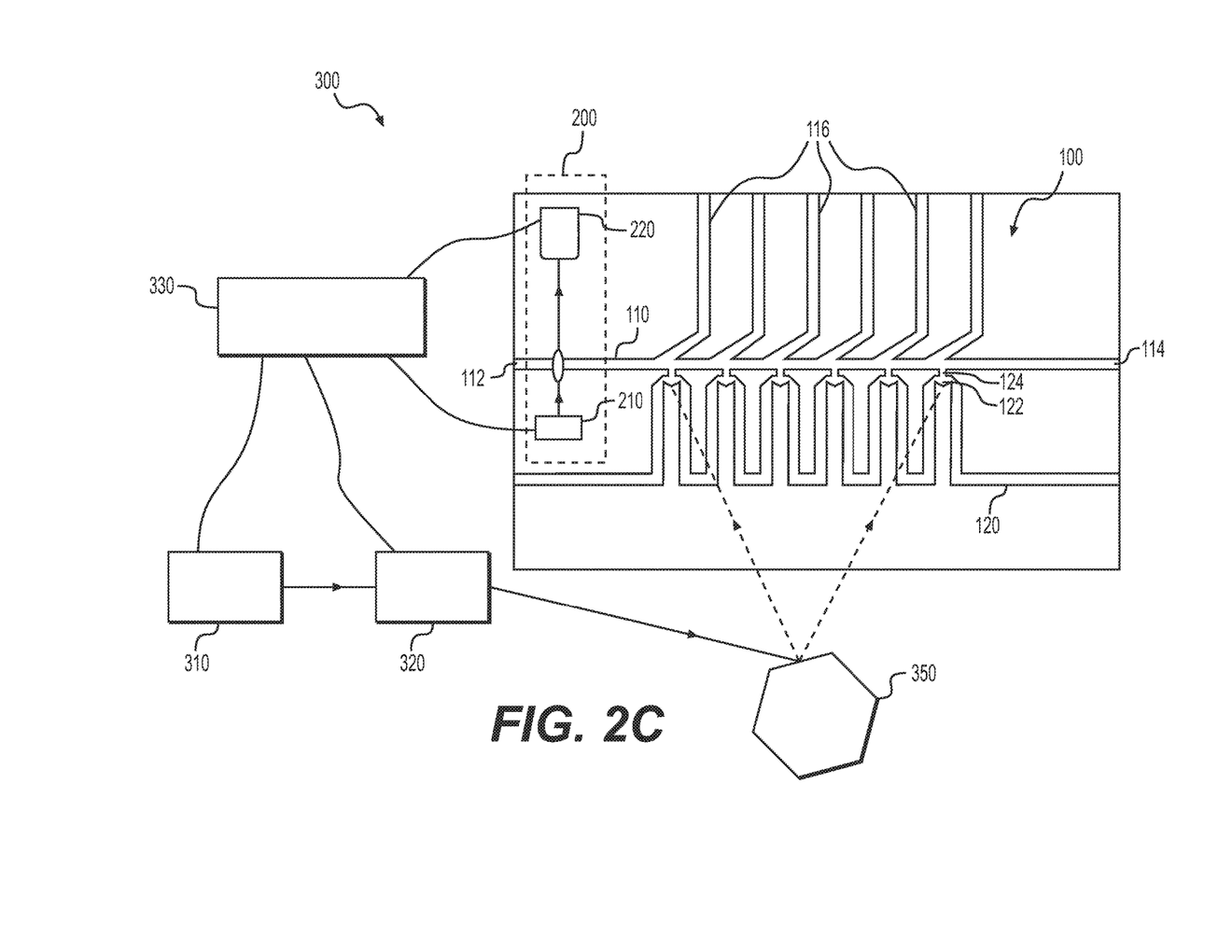
FIG. 2C is a schematic representation of another exemplary system for sorting particles, according to embodiments of the present disclosure.

In some applications, a range of angular deflection between that provided by AOM 320 and galvo mirror assembly 340 is needed. In such instances, a polygon mirror assembly may be used as the modulation device.

FIG. 2C is a schematic representation of another exemplary system 300 for sorting particles. As shown in FIG. 2C, the modulation device of system 300 may be a polygon mirror assembly 350. The rotation of polygon mirror assembly 350 allows the scanning of a laser beam across a linear range on microfluidic device 100 by deflecting the incoming laser beam by a multifaceted mirror. The angular deflection caused by polygon mirror assembly 350 may range up to 5 degrees and the scanning rate of polygon mirror assembly 350 may range up to tens of kilohertz.

In some embodiments, more than one modulation device may be used for directing the laser beam to a suitable actuation region in microfluidic device 100. For example, a pair of modulation devices operating in orthogonal dimensions may be cascaded to direct the laser beam to a spot in a two-dimensional area. For example, a first modulation device may be placed in close proximity to a second modulation device. Alternatively, a lens may be used to reimage a laser spot from the first modulation device to the second modulation device. The two modulation devices may be any combination of AOM 320, galvo mirror assembly 340, and polygon mirror assembly 350.

The high modulation or scanning rate of AOM 320, galvo mirror assembly 340, and/or polygon mirror assembly 350 allows dynamic direction of laser pulses to suitable actuation regions and thus the deflection of particles passing through sample channel 110 sequentially at a high speed, thereby allowing for high-throughput multiplexed sorting of particles.

As described herein, the optical switching system may further include other suitable optical elements for directing a continuous or pulsed laser beam from laser 310 to the modulation device, e.g., AOM 320, and optical elements for directing and focusing laser pulses to selected actuation regions 122. These optical elements may include one or more dichroic mirrors, lenses, objective, filters, beam dumps, etc.

As described above, before deflecting a particle to a target output channel 116, the particle passes by and is detected detection system 200, which determines a target output channel 116 to sort the particle into based on results of the detection. Controller 330 may use the detection results of particle 10 for controlling laser 310 and the modulation device for generating a laser pulse and/or for directing the laser pulse as described below in reference to FIG. 3.

Figure 3:
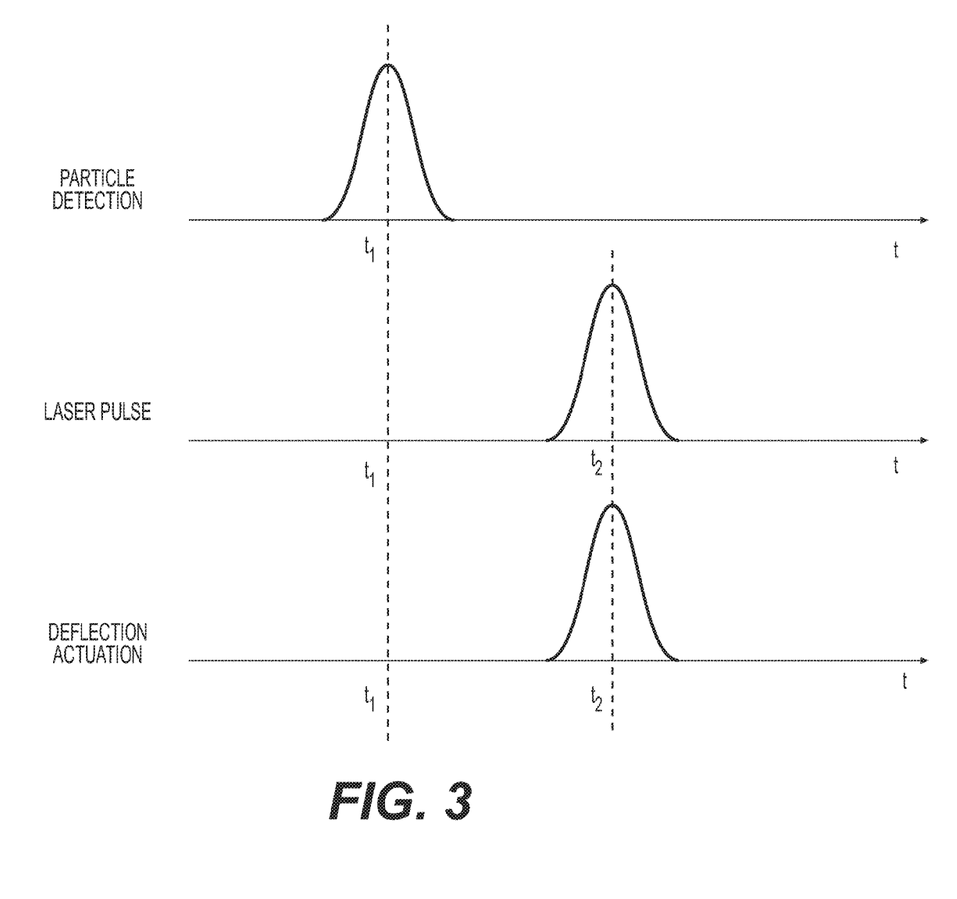
FIG. 3 is a graphical illustration for an exemplary timing of the operation of the exemplary systems of FIGS. 2A-2C, according to embodiments of the present disclosure.

FIG. 3 is a graphical illustration for an exemplary timing of the operation of the exemplary systems of FIGS. 2A-2C. As shown in FIG. 3, detection system 200 may detect the particle at a first time point ($t_1$) and determine whether the particle is desired to be sorted into a target output channel 116. Controller 330 may receive the results of detection of the particle from detection system 200, and determine which output channel 116 is the target output channel to sort the particle into. Controller 330 may then trigger a laser pulse for deflecting the particle at a second time point ($t_2$) with a suitable time delay, i.e., a time difference between $t_1$ and $t_2$. The time delay may be determined based on various factors, such as the distance of the location of particle detection, and the location of the junction between the sample channel and the target output channel, and the flow speed of the fluid medium carrying the particle.

As shown in FIG. 3, controller 330 may further synchronize the triggering of the laser pulse with the direction of the laser pulse by the modulation device, e.g., AOM 320, galvo mirror assembly 340, or polygon mirror assembly 350. For example, controller 330 may instruct the modulation device to direct the laser pulse to a suitable actuation region 122 corresponding to the target output channel 116 at the second time point ($t_2$). This allows the laser pulse to induce cavitation bubble at the suitable actuation region 122 at about the same time when the laser pulse is triggered, thereby reducing the potential actuation of other regions in actuation channel 120 while the modulation device is scanning across microfluidic device 100. This increases the accuracy of selectively deflecting the particles to desired output channels 116.

As described herein, the geometry of the channels and junctions of microfluidic device 100 may be configured as needed based on the application. Advantageously, the optical switching system, e.g., the modulation device, allows for rapidly modulating the direction of the laser pulse to deflect particles to target output channels 116 in a flexible and reconfigurable manner. The modulation device, e.g., AOM 320, galvo mirror assembly 340, and polygon mirror assembly 350, allows for actuation of any desired actuation region 122 corresponding to a target output channel 116 within its scanning range at any given time, thereby allowing the particles to be sorted to different output channels in any sequence. The total number of actuation regions 122 and output channels 116 that can be used may be determined by various factors, including the layout and dimensions of the microfluidic channels, and the resolution and range of angular deflection provided by the modulation device.

Figure 4:
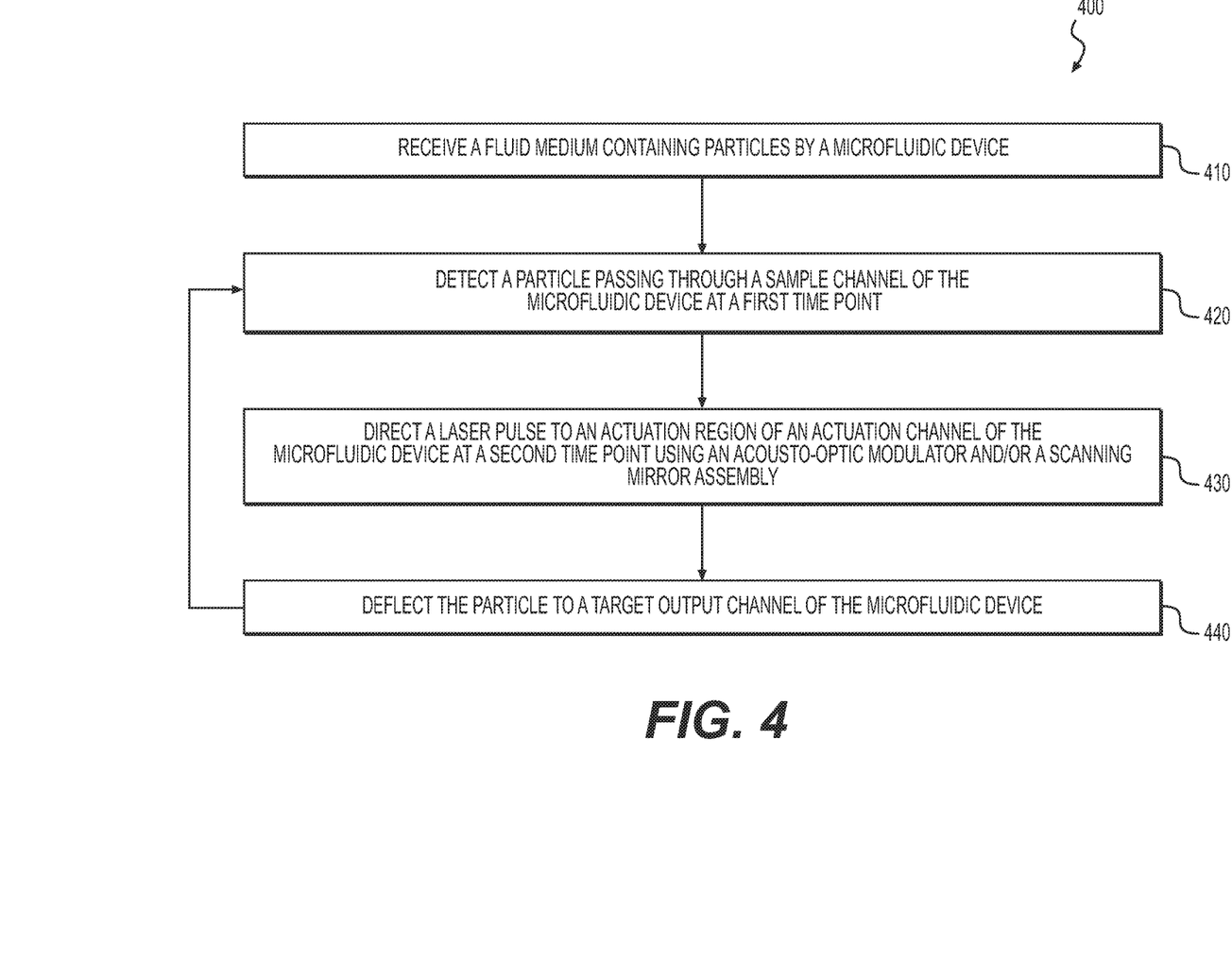
FIG. 4 is a flowchart of an exemplary method for sorting particles, according to embodiments of the present disclosure.

System 300 as described herein may be utilized in a variety of methods and devices for sorting particles. FIG. 4 is a flowchart of an exemplary method 400 for sorting particles. Method 400 uses system 300 and features of the embodiments of system 300 described above in reference to FIGS. 2A-2C and 3.

At step 410, a fluid medium containing or carrying a plurality of particles is received by microfluidic device 100. The fluid medium may pass through microfluidic device 100 through sample channel 110. At step 420, a particle passing through sample channel 110 may be detected by detection system 200 at a first time point. Detection system 200 may determine which target output channel 116 in the microfluidic device 100 to sort the detected particle into based on the detection results. Alternatively, the detection results may be sent by detection system 200 to controller 330, which then determines a target output channel 116. At step 430, a pulsed laser beam or a laser pulse is directed by a modulation device to an actuation region 122 in actuation channel 120 in the microfluidic device 100 at a second time point. The modulation device may be an AOM or a scanning mirror assembly. At step 440, the particle is deflected towards a target output channel when the laser pulse induces a cavitation bubble that creates a high speed liquid jet into sample channel 110. Steps 430 and 440 may be synchronized using a controller 330. Controller 330 may control the timing of the operation of detection system 200 and the optical switching system as described above.

After a particle is deflected to a target output channel at step 440, method 400 may go back to step 420 to deflect another particle in the fluid medium to a suitable target output channel. As described above, the optical switching system used by method 400 allows for rapid scanning or deflecting of laser pulses in a flexible and reconfigurable manner. Thus, method 400 advantageously allows for dynamic and multiplexed sorting of a mixture of particles into desired subpopulations.

Various embodiments of method 400 may include one or more of the following features or steps. For example, if the laser used by method 400 is a continuous wave laser, method 400 may include generating a pulsed laser beam from a continuous wave laser beam received from the laser using an AOM. Method 400 may further include determining a suitable actuation region 122 in the actuation channel 120 based on the detection results and the geometry of the microfluidic device 100. In some embodiments, method 400 may further include modulating the direction of a pulsed laser beam or a laser pulse using a pair of modulation devices configured in series and operating in orthogonal dimensions, such as an AOM and a scanning mirror assembly.

In some embodiments, controller 330 may have a processor and one or more computer-readable media that store instructions or operational steps. The instructions or operational steps, when executed by the processor, may operate the detection system and the optical switching system. The computer-readable medium may further store instructions or operational steps that, when executed by the processor, perform the steps of method 400.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware and software, but systems and methods consistent with the present disclosure can be implemented as hardware alone. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

Instructions or operational steps stored by a computer-readable medium may be in the form of computer programs, program modules, or codes. As described herein, computer programs, program modules, and code based on the written description of this specification, such as those used by the controller, are readily within the purview of a software developer. The computer programs, program modules, or code can be created using a variety of programming techniques. For example, they can be designed in or by means of Java, C, C++, assembly language, or any such programming languages. One or more of such programs, modules, or code can be integrated into a device system or existing communications software. The programs, modules, or code can also be implemented or replicated as firmware or circuit logic.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. A system for sorting particles, the system comprising:
   a microfluidic device comprising:
      a sample channel for passing through the particles in a fluid medium;
      a plurality of output channels fluidly connected to the sample channel at a plurality of junctions offset from each other along a length of the sample channel; and
      an actuation channel;
   a detection system that detects a given particle of the particles passing through the sample channel; and
   an optical switching system that deflects the given particle toward a target output channel based on results detected by the detection system, the optical switching system including a modulation device configured to direct a laser pulse to an actuation region in the actuation channel corresponding to the target output channel.

2. The system of claim 1, wherein the actuation channel comprises:
   a plurality of actuation regions, including the actuation region, offset from each other along the actuation channel and each corresponding to one of the junctions; and
   a plurality of outlets connecting the actuation regions to the sample channel, the outlets being located adjacent to the junctions of the output channels and the sample channel.

3. The system of claim 1, wherein the detection system comprises an illumination source and at least one photodetector.

4. The system of claim 1, wherein the laser pulse is configured to induce a cavitation bubble that expands in the actuation region, deflecting the given particle to the target output channel.

5. The system of claim 1, wherein the optical switching system further comprises at least one optical element configured to focus the laser pulse to the actuation region.

6. The system of claim 1, wherein the optical switching system further comprises a pulsed laser that generates the laser pulse.

7. The system of claim 1, wherein the optical switching system comprises:
   a continuous wave laser, to generate a laser beam; and
   an acousto-optic modulator disposed relative to the continuous wave laser to receive the laser beam from the continuous wave laser and to pulse the laser beam to generate the laser pulse.

8. The system of claim 1, wherein the modulation device is an acousto-optic modulator.

9. The system of claim 1, wherein the modulation device is a scanning mirror assembly.

10. The system of claim 9, wherein the scanning mirror assembly is a galvo mirror assembly.

11. The system of claim 9, wherein the scanning mirror assembly is a polygon mirror assembly.

12. The system of claim 1, further comprising a controller that controls the timing of the operations of the detection system and the optical switching system such that the optical switching system directs the laser pulse to the actuation region with a suitable time delay from the detection of the given particle.

13. The system of claim 12, wherein the controller further synchronizes triggering of the laser pulse and the direction of the laser pulse to the actuation region.

14. The system of claim 1, wherein the actuation channel runs proximate to the sample channel between two bends in the actuation channel, and wherein the actuation region is disposed between the two bends in the actuation channel.

15. The system of claim 14, wherein the actuation region comprises a reservoir defined by a widening of the actuation channel between the two bends and includes an outlet connecting the reservoir to the sample channel.

16. A method for sorting particles, the method comprising:
   receiving a fluid medium containing the particles by a microfluidic device, the microfluidic device comprising:
      a sample channel for passing through the particles;
      a plurality of output channels fluidly connected to the sample channel at a plurality of junctions offset from each other along a length of the sample channel; and
      an actuation channel;
   detecting a given particle of the particles passing through the sample channel using a detection system at a first time point;
   determining a target output channel at a location within the length based on results detected by the detection system;
   directing a laser pulse to an actuation region in the actuation channel corresponding to the target output channel at a second time point; and
   deflecting the given particle toward the target output channel by inducing a cavitation bubble that expands in the actuation region using the laser pulse.

17. The method of claim 16, wherein the actuation channel comprises:
   a plurality of actuation regions, including the actuation region, offset from each other along the actuation channel and each corresponding to one of the junctions; and
   a plurality of outlets connecting the actuation regions to the sample channel, the outlets being located adjacent to the junctions of the output channels and the sample channel.

18. The method of claim 16, further comprising triggering the laser pulse, in synchrony with the directing of the laser pulse.

19. The method of claim 16, further comprising directing the laser pulse using at least one acousto-optic modulator.

20. The method of claim 16, further comprising generating the laser pulse from a continuous wave laser using an acousto-optic modulator.

21. The method of claim 16, further comprising directing the laser pulse using at least one scanning mirror assembly.

22. The method of claim 21, wherein the at least one scanning mirror assembly is a galvo mirror assembly.

23. The method of claim 21, wherein the at least one scanning mirror assembly is a polygon mirror assembly.

24. The method of claim 16, further comprising directing the laser pulse using at least one acousto-optic modulator and at least one scanning mirror assembly that direct the laser pulse in orthogonal dimensions.

25. The method of claim 16, further comprising focusing the laser pulse to the actuation region.

26. The method of claim 16, further comprising directing the laser pulse away from the actuation region based on results detected by the detection system.

27. A system for sorting particles, the system comprising:
a microfluidic device comprising:
   a sample channel for passing through the particles in a fluid medium;
   a plurality of output channels fluidly connected to the sample channel at a plurality of junctions offset from each other across a linear range on the microfluidic device; and
   an actuation channel;
a detection system that detects a given particle of the particles passing through the sample channel; and
an optical switching system that deflects the given particle toward a target output channel based on results detected by the detection system, the optical switching system including an acousto-optic modulator configured to redirect a laser pulse to an actuation region in the actuation channel corresponding to the target output channel.

28. The system of claim 27, wherein the actuation channel comprises:
a plurality of actuation regions, including the actuation region, offset from each other along the actuation channel and each corresponding to one of the junctions; and
a plurality of outlets connecting the actuation regions to the sample channel, the outlets being located adjacent to the junctions of the output channels and the sample channel.

29. The system of claim 27, wherein the detection system comprises an illumination source and at least one photodetector.

30. The system of claim 27, wherein the laser pulse is configured to induce a cavitation bubble that expands in the actuation region, deflecting the given particle to the target output channel.

31. The system of claim 27, wherein the optical switching system further comprises at least one optical element configured to focus the laser pulse to the actuation region.

32. The system of claim 27, further comprising a controller that controls the timing of the operations of the detection system and the optical switching system such that the optical switching system directs the laser pulse to the actuation region with a suitable time delay from the detection of the given particle.

33. The system of claim 32, wherein the controller further synchronizes triggering of the laser pulse and the direction of the laser pulse to the actuation region.

34. The system of claim 27, wherein the optical switching system further comprises a pulsed laser that generates the laser pulse.

35. The system of claim 27, further comprising a continuous wave laser, wherein the laser pulse is generated by pulsing a laser beam from the continuous wave laser using the acousto-optic modulator.

* * * * *